US009964386B2

(12) United States Patent
Teetzel

(10) Patent No.: US 9,964,386 B2
(45) Date of Patent: May 8, 2018

(54) PROJECTILE SYSTEM WITH ENVIRONMENTAL HAZARD SENSING

(71) Applicant: WILCOX INDUSTRIES CORP., Portsmouth, NH (US)

(72) Inventor: James W. Teetzel, Portsmouth, NH (US)

(73) Assignee: Wilcox Industries Corp., Newington, NH (US)

( * ) Notice: Subject to any disclaimer, the term of this patent is extended or adjusted under 35 U.S.C. 154(b) by 144 days.

(21) Appl. No.: 14/792,961

(22) Filed: Jul. 7, 2015

(65) Prior Publication Data

US 2016/0010967 A1 Jan. 14, 2016

Related U.S. Application Data

(60) Provisional application No. 62/022,487, filed on Jul. 9, 2014.

(51) Int. Cl.
*F42B 15/08* (2006.01)
*F42B 5/02* (2006.01)
(Continued)

(52) U.S. Cl.
CPC ................ *F42B 15/08* (2013.01); *F42B 5/02* (2013.01); *F42B 5/10* (2013.01); *F42B 10/14* (2013.01);
(Continued)

(58) Field of Classification Search
CPC ........... G01N 33/0004; G01N 33/0006; G01N 33/0073; G01N 33/0075; G01V 3/12; G07C 5/008; G08B 21/18; G08B 21/182; F42B 5/02; F42B 5/10; F42B 10/02; F42B 10/14; F42B 10/60; F42B 10/62; F42B 10/64;
(Continued)

(56) References Cited

U.S. PATENT DOCUMENTS 3,651,395 A * 3/1972 Owen ...................... G01V 3/12 324/337
3,751,984 A * 8/1973 Rennie ............... G01N 33/0075 436/181

(Continued)

FOREIGN PATENT DOCUMENTS

EP 1113268 A1 * 7/2001 ......... G01N 33/0075
FR 2438877 A1 * 5/1980 ............. G07C 5/008
FR 2754911 A1 * 4/1998 ......... G01N 33/0075

*Primary Examiner* — Bernarr E Gregory
(74) *Attorney, Agent, or Firm* — McLane Middleton, Professional Association

(57) ABSTRACT

In one aspect, a modular air sampling system includes a sensor module defining a nose, the sensor module including a sensor for sampling contaminants in the atmosphere. A processing and sending module includes processing electronics in communication with the sensor for receiving a signal from the sensor representative of sampled contaminants in the atmosphere. The processing and sending module further includes a radio frequency transmitter operably coupled to the processing electronics for transmitting a radio frequency signal representative of one or more contaminants sensed by the sensor. In another aspect, a modular air sampling system includes a sensor module containing the sensor, processing electronics, and radio frequency transmitter within the sensor module housing.

36 Claims, 9 Drawing Sheets

(51) Int. Cl.

| | |
|---|---|
| ***F42B 5/10*** | (2006.01) |
| ***F42B 10/14*** | (2006.01) |
| ***F42B 10/64*** | (2006.01) |
| ***F42B 15/01*** | (2006.01) |
| ***G08B 21/18*** | (2006.01) |
| ***G01N 33/00*** | (2006.01) |
| *F42B 15/00* | (2006.01) |

(52) U.S. Cl.
CPC ......... *F42B 10/64* (2013.01); *G01N 33/0075* (2013.01); *F42B 15/01* (2013.01); *G08B 21/182* (2013.01)

(58) Field of Classification Search
CPC .......... F42B 15/01; F42B 15/08; F42B 12/38; B64G 1/1021
See application file for complete search history.

(56) References Cited

U.S. PATENT DOCUMENTS

| | | | | |
|---|---|---|---|---|
| 4,402,480 | A * | 9/1983 | Udell | B64G 1/1021 |
| H489 | H * | 7/1988 | Brodman et al. | F42B 12/38 |
| 2011/0163892 | A1* | 7/2011 | Groves | G01N 33/0075 340/901 |
| 2015/0247714 | A1 | 9/2015 | Teetzel et al. | |

* cited by examiner

PROJECTILE SYSTEM WITH ENVIRONMENTAL HAZARD SENSING

CROSS REFERENCE TO RELATED APPLICATION

This application claims priority to U.S. provisional application No. 62/022,487 filed Jul. 9, 2014, which is incorporated herein by reference in its entirety.

INCORPORATION BY REFERENCE

This application is also related to U.S. Provisional Application No. 61/638,368 filed Apr. 25, 2012, and U.S. Nonprovisional application Ser. No. 13/870,340 filed Apr. 25, 2013. Each of the aforementioned applications is incorporated herein by reference in its entirety.

BACKGROUND

The present disclosure relates generally to a projectile system and method for detecting gaseous materials present in the atmosphere at a remote location. The present system and method find particular utility in sensing chemical and/or biological threats in atmospheric air at specific distances or locations for tactical or military defense purposes. It will be recognized, however, that the present development may also be used to identify and provide distance and location information for chemical or biological hazards in connection with natural disasters, industrial spills, leaks, or accidents, and so forth. One advantage of the present system resides in its ability to identify potential chemical or biological hazards from a remote location, thus allowing the user to best plan for use of protective equipment that the user may have at his or her disposal, such as respirator masks, self-contained breathing apparatuses, protective clothing, etc. In preferred embodiments, the environmental hazard sensing projectile system herein can be adapted for firing from preexisting launch platforms, thus reducing costs and facilitating deployment.

SUMMARY

In one aspect, a modular projectile system comprises a chemical and/or biological sensing module defining a nose of the projectile. A flight control module is removably attachable to the sensor module and includes a plurality of airfoils, the airfoils being moveable between a refracted state and an extended state. A processing module is removably attached to the flight control module for receiving the sensor data from the sensor module and transmitting sensed chemical or biological hazard information cross-referenced with flight time and/or geolocation information to a radio receiver or communication network associated with the user. A rocket module is attached to the processing module and includes a rocket motor configured to propel the modular projectile system. A cartridge module is provided, which includes a charge of explosive material to propel the projectile system out of a launch tube or barrel of the launch platform.

In another aspect, a modular projectile system comprises a unitary or combined chemical and/or biological sensing and processing module which is configured to be attached to a cartridge module with or without a rocket motor.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
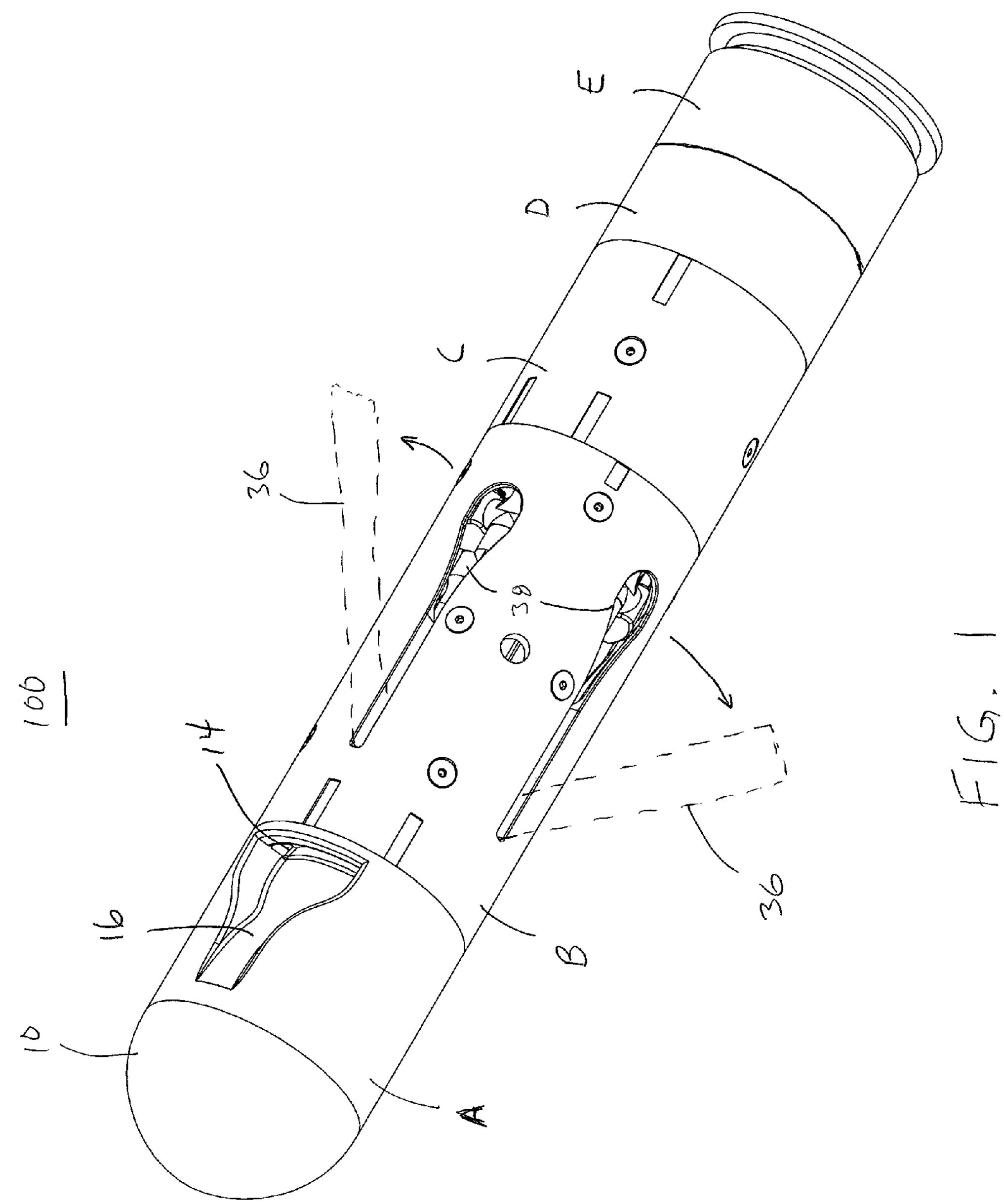
FIG. 1 is an isometric view of a modular projectile system in accordance with a first exemplary embodiment of the present disclosure, wherein the wings appear in the folded position.
Figure 2:
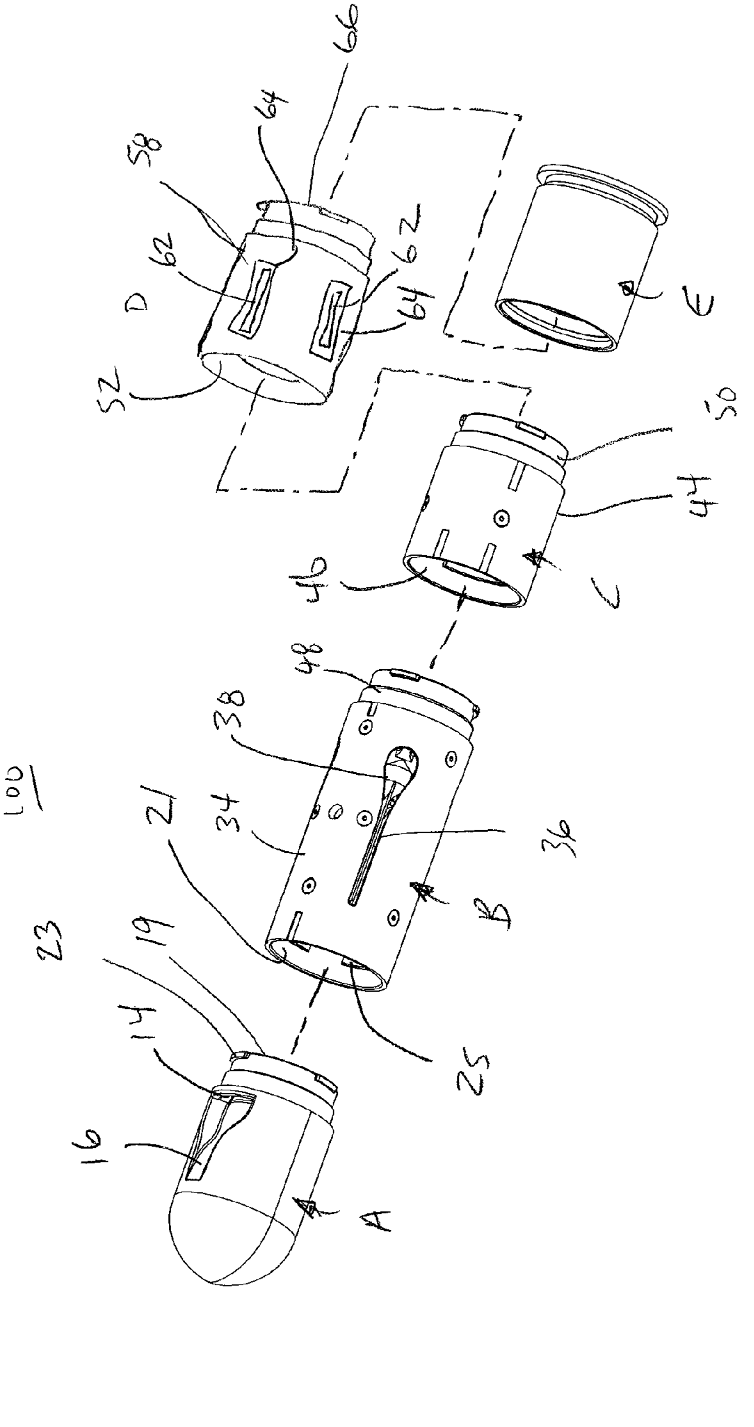
FIG. 2 is an isometric exploded view of the modular projectile system appearing in FIG. 1.
Figure 3:
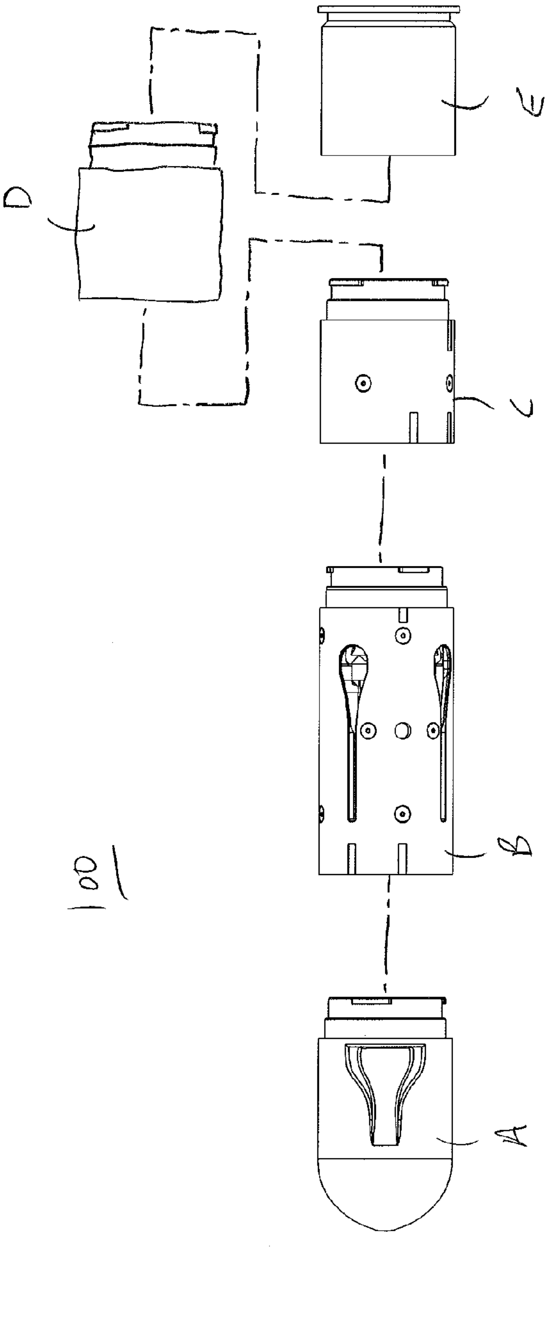
FIG. 3 is an exploded side elevational view of the modular projectile system appearing in FIG. 1.
Figure 4:
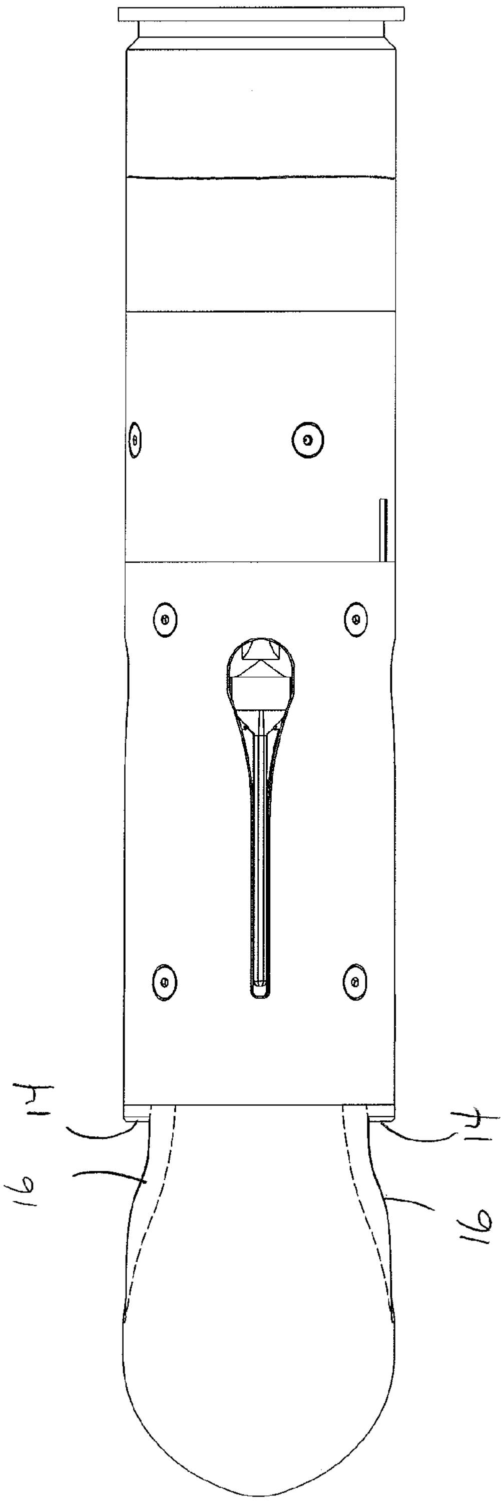
FIG. 4 is a side elevational view of the modular projectile system appearing in FIG. 1, wherein the housing of the sensor module is removed, illustrating the dual air duct design of the preferred embodiment.
Figure 5:
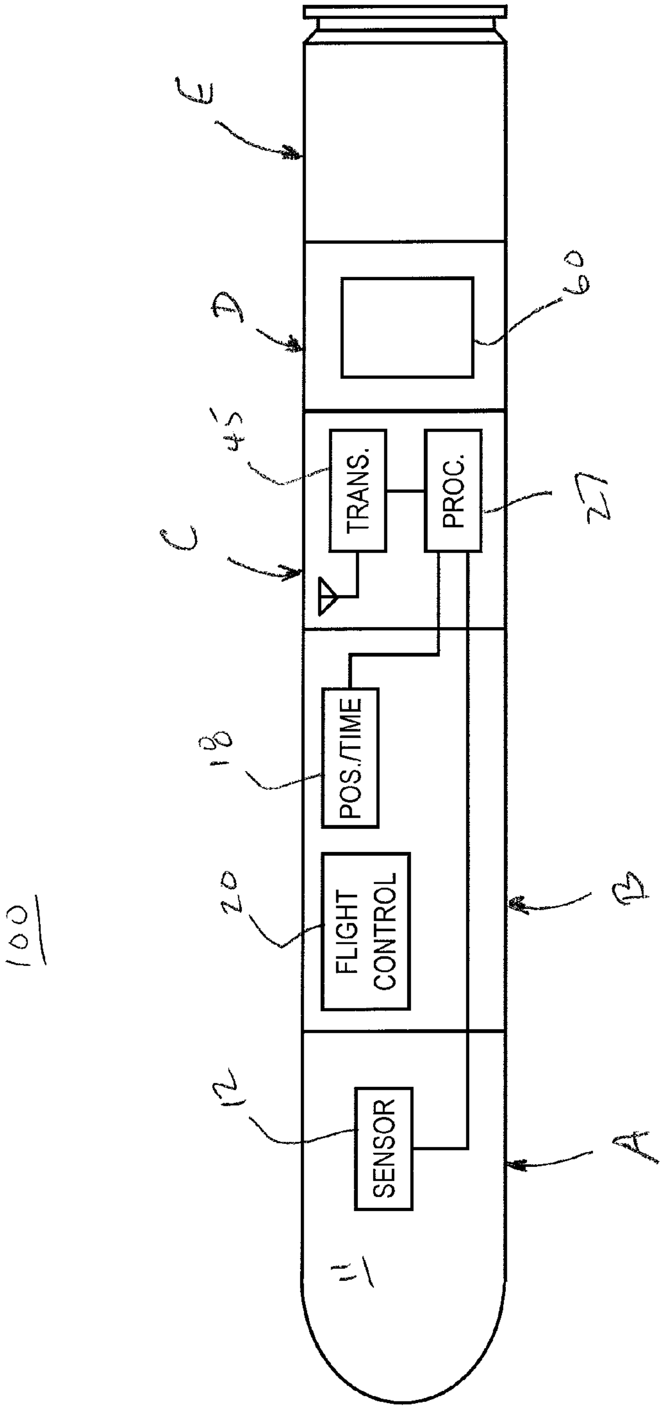
FIG. 5 is a block diagram of the embodiment appearing in FIG. 1.

Referring now to FIGS. 1-5, there is shown an exemplary modular air sampling system 100, which includes a sensor module A, a flight control module B, a processing and sending module C, a motor or rocket booster module D, and a cartridge shell E.

The sensor module A includes a generally rounded, conical or otherwise tapered outer shell construction 10 shaped to minimize aerodynamic resistance and defining a nose cone of the rocket system 100. The sensor module A includes an interior cavity or compartment 11 housing one or more chemical or biological sensors 12. Such sensors include electrochemical sensors, metal oxide semiconductor sensors, spectroscopic gas sensors, and so forth. The one or more sensors 12 may include an array of sensors configured to detect a broad range of biological and/or chemical contaminants. Alternatively, the sensor(s) 12 could be configured to sense a one or a limited number of biological and/or chemical contaminants. For example, a system could be provided with a plurality of different sensor modules A each having different sensing capabilities, wherein the sensor module A can be selected for a particular application based on a biological or chemical contaminant that is expected in a given area or situation.

The sensor module A includes a pair of air intake ducts 14. The ducts 14 are disposed on opposite sides of the module A. Each duct 14 includes an adjacent air flow directing surface 16. The air flow directing surfaces 16 may have an airfoil-like shape and are configured to direct a flow of air through the ducts 14 and into the interior compartment of the sensor module A where it impinges on the one or more sensors 12. The air flow directing surfaces 16 may configured as a so-called submerged inlet, NACA duct or NACA scoop, or other low drag air inlet configured to allow air to flow into the ducts 14 where it contacts the one or more sensors 12.

The module A includes a rear connector 19 which is complementary with and removably attachable to a forward facing connector 21 on the flight control module B. The rear connector 19 and the forward connector 21 may include complementary and aligned facing surfaces. In the illustrated embodiment, the rear connector 19 includes keyed projections 23 which are received in complementary openings, channels or grooves (see FIG. 3) to allow the units A, B to be inserted and then twisted into the locked position. Other bayonet or keyed connections are contemplated. In certain embodiments, markings or indicia may be provided on adjacent modules to show proper alignment as described in the aforementioned commonly owned U.S. application Ser. No. 13/870,340.

In certain embodiments, an electrical interface is provided within the forward and rear connectors 19, 21 to provide a conductive pathway for sending an electrical signal to a processing unit 27 in the processing and sending module C when the modules A, B, and C are connected properly. The electrical connections between adjacent attached members may also be provided to ensure that a given rocket construction prepared using the present modular components comprises a proper configuration of modules. In a preferred embodiment, the electrical connections between the adjacent modules serve as an interlock mechanism preventing the system 14 from booting up unless the attached components are properly attached and in a proper configuration. Alternatively, or in addition, the keyed projections 23 and receptacles 25 on the connecting ends of each module may be keyed with distinct geometry to inhibit the improper attachment or combination of modules.

The flight control module B includes a generally cylindrical outer shell housing 34 receiving a plurality of airfoils or wings 36 circumferentially spaced about the flight control module B. The wings 36 can be folded into receptacles 38 in the body of the flight control module B to allow the assembled system 100 to fit into a launch platform, which is discussed below, prior to launch of the unit 100. As seen in FIG. 1, when the wings 36 are in the folded state, the wings 36 are received in the openings 38 in the body of the module B.

The flight control module B may also include a positioning system 18, which may be an absolute or relative positioning system. Exemplary positioning systems include, for example, a navigational system, such as Global Positioning System (GPS) based systems, Global Navigation Satellite System (GLONASS) based systems, etc., inertial systems, etc. In alternative embodiments, the positioning system 18 may employ a clock to record time of flight. In this manner, the relative position of the unit 100, e.g., the distance from the user at a given time, can be calculated based on time of flight and known trajectory or ballistic characteristics of the unit 100. In still further embodiments, the positioning system 18 may include an accelerometer provided to count the number of axial rotations of the unit 100 during flight, wherein the distance of the unit 100 from the user at a given time can be calculated based on the number of rotations and known trajectory or ballistic characteristics of the unit 100. In certain embodiments, the flight control module B also includes a guidance control computer or processor 20 for guiding the rocket system along a programmed fight path.

In certain embodiments, the flight control module B includes a flight control processor 20 and an associated electronic memory operably coupled thereto for storage and execution of flight control instructions or algorithms.

After firing, the wings 36 can be moved to their extended position, as shown in the broken lines appearing in FIG. 1. Each of the wings 36 is independently controllable and may be rotated or tilted as ailerons to provide maneuverability/steering control as well as stability of the sensing system during flight. The wings 36 are small enough to fit within the housing shell 34 to allow the system 100 to fit within the constraints of the launching platform while providing the ability to allow the system 100 to perform banking and turning maneuvers during flight and, in preferred embodiments, are large enough to steer the rocket system 100 around obstacles during flight. Additionally or alternatively, the system 100 may be maneuvered by a conventional thrust vector control system, e.g., of the type using a gimbaled booster nozzle to steer the weapon. The wings 36 may be actuated and controlled via springs, hydraulics, pneumatics, motors, and so forth.

The processing/sending module C houses the processing unit 29 and a radio frequency (RF) transmitter or transceiver 45 and includes an outer shell 44, a front connector 46 for removable attachment to a rear connector 48 of the flight control module B, and a rear connector 50 for connection to a front connector 52 of the booster module D. The manner of connection may be generally as detailed above, and the connectors may in include the projections 23 and complementary receivers 25 as detailed above, although the geometry of the connection may be different to avoid attaching the modules improperly, e.g., in terms of sequence or compatibility.

Electrical connections are provided between the attached modules A, B, and C for transmission of data to the RF transmitter/transceiver 45. The processor 20 receives raw sensor data from the sensor 12, which can be correlated with positional data from the positioning system 18 (or alternatively time of flight or spin count data) to identify the presence (and optionally concentration) of an identified airborne hazard and to provide a signal representative of the same correlated to position and/or distance from the user. The position- and/or distance-correlated contaminant data is transmitted via the transmitter 45 to an RF receiver associated with the user. In certain embodiments, the RF receiver may be a radio frequency receiver contained within a life support unit. The received data may be output to a human viewable display. Information concerning the identity and position/distance of airborne hazards allows the user to best use the breathing devices at his or her disposal.

The housing shells, wings, vanes, etc., of the present system may be formed of a metal or metal alloy material or a composite material comprising a fiber reinforced polymer material as are known in the aerospace industry.

The rocket booster module D includes an outer shell housing 58 defining a rocket motor configured with a rocket-based propulsion system 60 as would be generally known in the art. The rocket motor 60 may be powered by any suitable rocket fuel in any suitable form, including solid, liquid, gel, or any combination thereof. In certain embodiments, a plurality of retractable air vanes or fins 62 are folded into receptacles 64 in the housing shell 58 and are extended for stability during flight. In certain embodiments or configurations, the rocket module D may be provided with fixed vanes or fins.

In certain embodiments, the rocket system 100 may be configured to be fired from a standard or conventional launch platform, such as a grenade launcher 250 (see FIG. 9), e.g., a single shot 40 mm grenade launcher. The rearward end 66 of the motor module D is received within a 40 mm shell casing or cartridge E, which includes a charge of explosive material to propel the rocket system 100 out of the launch tube of the launch platform. In certain embodiments, the charge may be relatively small, since for rocket boosted configurations it is only necessary to launch the rocket system 100 a sufficient distance away from the operator to safely fire the rocket motor D. In alternative embodiments, the rocket motor may be omitted and a larger charge of explosive material in the cartridge E may be used.

In preferred embodiments, the launch platform is an M320 grenade launcher module, although it will be recognized that the present system may be adapted for use with other calibers and/or launch platforms, including shoulder fired, stationary, etc.

Figure 6:
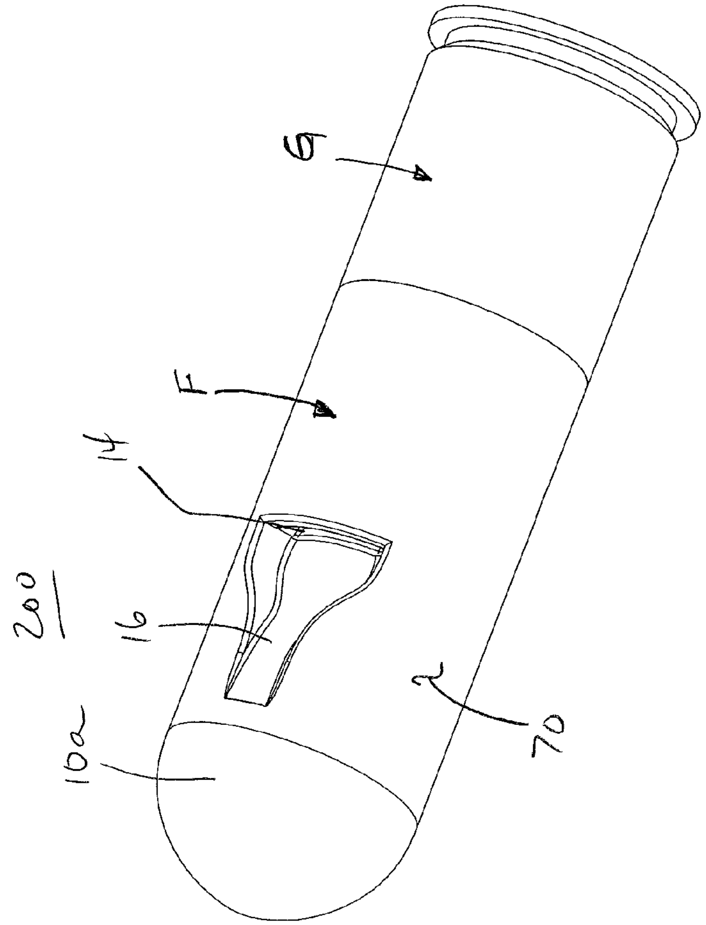
FIG. 6 is an isometric view of a modular projectile system in accordance with a second exemplary embodiment.
Figure 7:
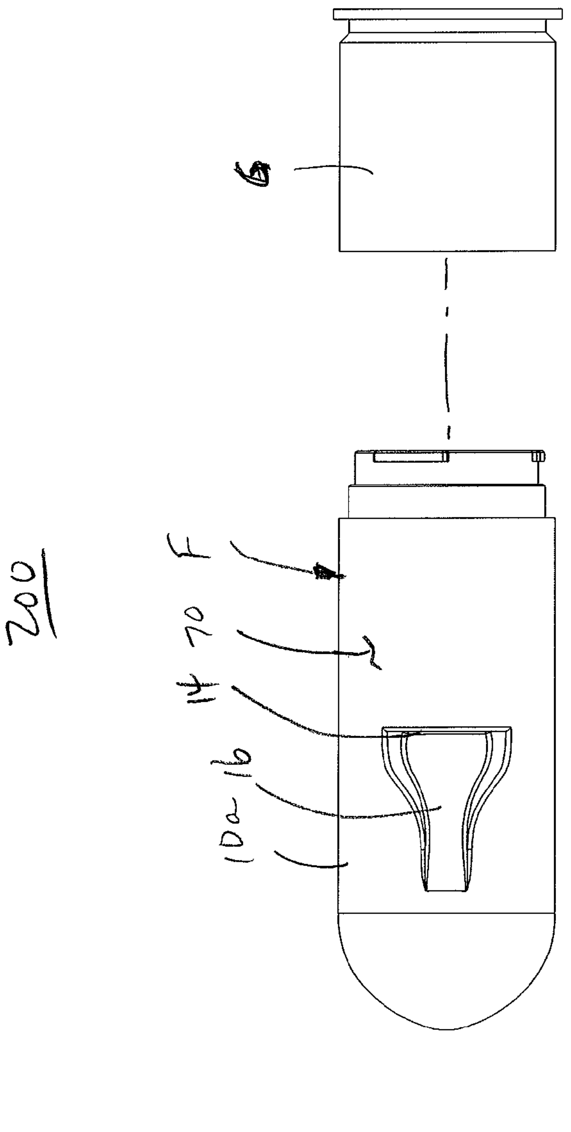
FIG. 7 is an exploded side elevational view of the modular projectile system appearing in FIG. 6.
Figure 8:
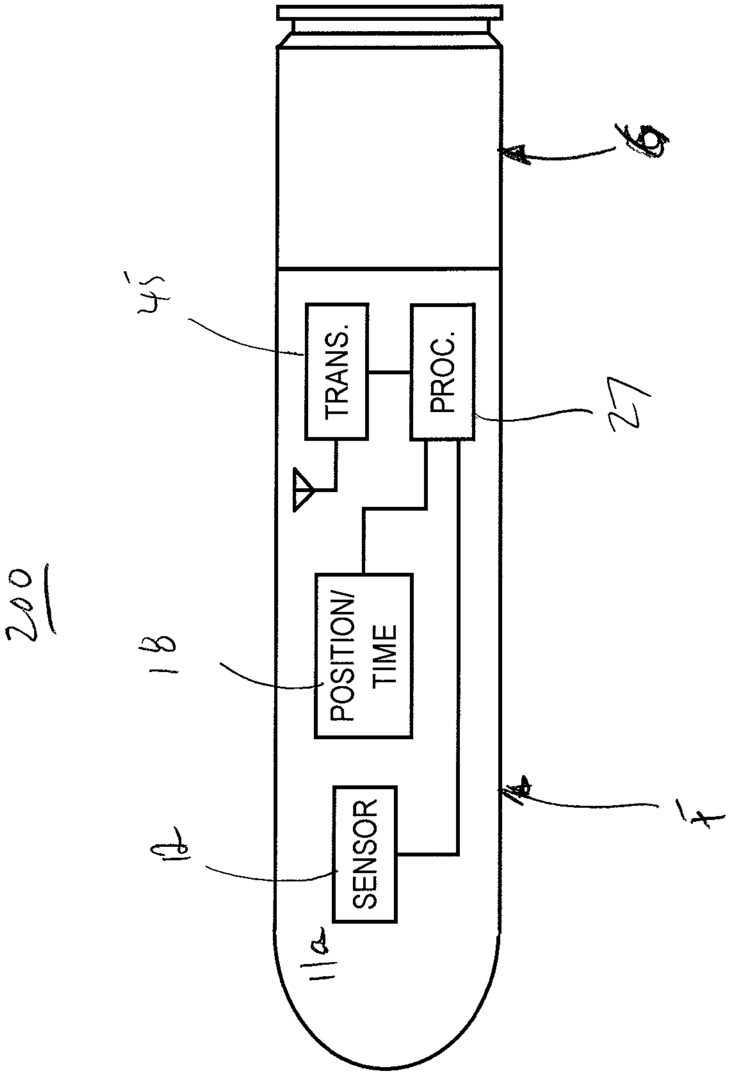
FIG. 8 is a block diagram of the embodiment appearing in FIG. 6.

FIGS. 6-8 illustrate an alternative embodiment sensing projectile system 200 wherein the sensor module 10 of the sensor module A as described above, and the position and/or timing module 18 of the flight control module B as described above, and the processor 27 and RF transmitter 45 of the processing/sending unit C as described above are combined into a single module F, wherein the above described hardware modules are within a single housing 70. The module F is attached to shell cartridge or casing G, such as a 40 mm cartridge casing or shell. The casing G differs from that casing E described above by way of the system 100 in that the casing F is configured to contain a larger explosive charge, in that the charge needs to be sufficient to launch the sensing projectile system 200 to the desired remote location where air sampling is desired to occur.

Figure 9:
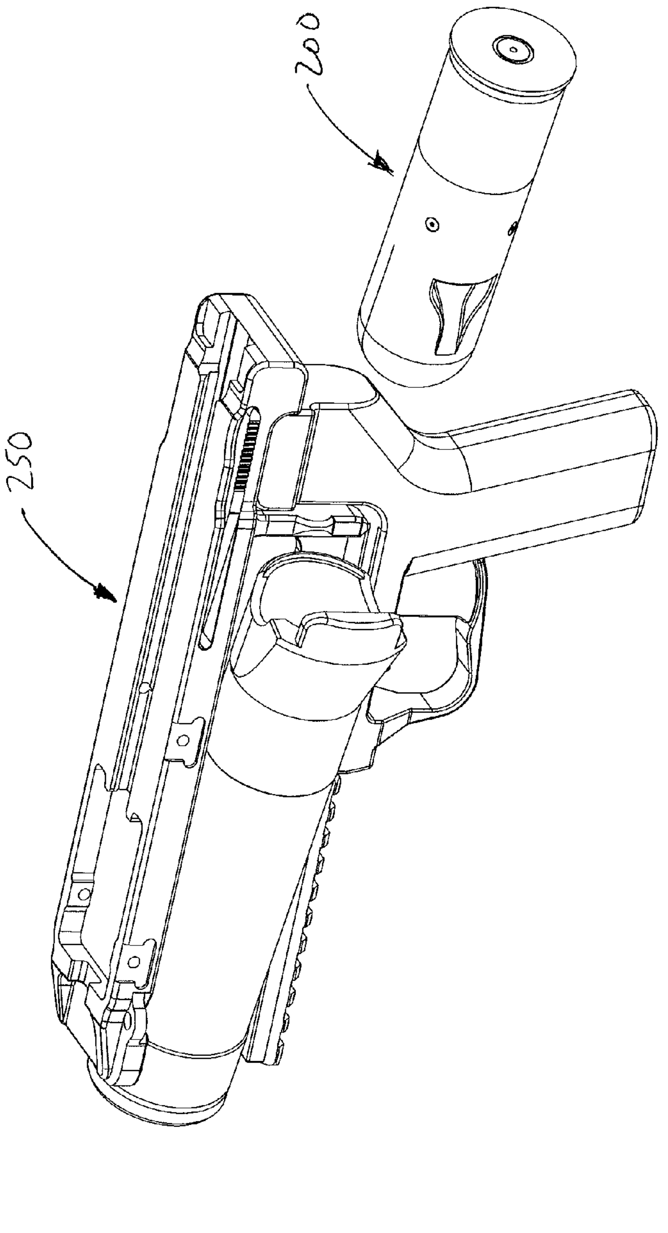
FIG. 9 illustrates the projectile system of FIG. 6 with a launch platform.

Referring now to FIG. 9, there is shown a grenade launcher 250. The sensing systems 100, 200 herein are advantageous in that they can be adapted for use with an existing launch platform, such as grenade launcher 250. Advantageously, the grenade launcher 250 is based on the M320 platform and preferably the Heckler & Koch HK M320. However, it is also contemplated that the modular air sampling system of this disclosure could be adapted for use with other standard launch platforms or with a custom or dedicated launch platform. In certain embodiments having retractable wings, such as the steering wings 36 or the stabilizing wings 62, a safety interlock may be provided for preventing movement of said wings to the extended state when the modular air sampling system is received in a launch platform.

The invention has been described with reference to the preferred embodiments. Obviously, modifications and alterations will occur to others upon reading and understanding the preceding detailed description. It is intended that the invention be construed as including all such modifications and alterations.

What is claimed is:

1. A modular air sampling system, comprising:

a sensor module defining a nose, said sensor module including a sensor for sampling contaminants in the atmosphere;

a processing and sending module including processing electronics in communication with the sensor for receiving a signal from the sensor representative of sampled contaminants in the atmosphere, said processing and sending module further including a radio frequency transmitter operably coupled to the processing electronics for transmitting a radio frequency signal representative of one or more contaminants sensed by the sensor; and a shell casing and a propelling charge contained within the shell casing for firing the modular air sampling system.

2. The modular air sampling system of claim 1, wherein the sensor module includes a housing, said housing including one or more inlets allowing ambient air to pass into the interior of the housing.

3. The modular air sampling system of claim 1, further comprising one or more air directing surfaces for directing ambient air into each of the one or more inlets.

4. The modular air sampling system of claim 1, further comprising a flight control module attached to the sensor module and containing a flight control system for guiding said air sampling system toward a target.

5. The modular air sampling system of claim 4, further comprising:

said flight control module removably attachable to the sensor module; and said flight control module including a plurality of airfoils, said airfoils being moveable between a retracted state and an extended state.

6. The modular air sampling system of claim 4, further comprising a rocket module attached to the processing and sending module, said rocket module including a rocket motor configured to propel the modular air sampling system.

7. The modular air sampling system of claim 4, further comprising:

one or both of a position sensor and a time-of-flight sensor received within the flight control module and operatively coupled to the processing electronics, said processing electronics configured to correlate one or both of a time and a geographic location with the signal from the sensor representative of sampled contaminants in the atmosphere.

8. The modular air sampling system of claim 4 further comprising a data bus received within the flight control module for communicating sensor data to the processing electronics.

9. The modular air sampling system of claim 1, further comprising:

one or both of a position sensor and a time-of-flight sensor operatively coupled to the processing electronics, said processing electronics configured to correlate one or both of a time and a geographic location with the signal from the sensor representative of sampled contaminants in the atmosphere.

10. The modular air sampling system of claim 1, further comprising a rocket module attached to the processing and sending module, said rocket module including a rocket motor configured to propel the air sampling system.

11. The modular air sampling system of claim 10, wherein the rocket module includes a plurality of vanes for providing stability during flight.

12. The modular air sampling system of claim 10, wherein said rocket motor is powered by a rocket fuel material in a form selected from the group consisting of a solid, a liquid, a gel, or any combination thereof.

13. The modular air sampling system of claim 10, wherein the rocket module is removably attached to the processing and sending module.

14. The modular air sampling system of claim 10, further comprising:

said shell casing attached to a rearward end of the rocket module, said shell casing including a charge of explosive material configured to propel the modular air sampling system a distance prior to said rocket motor being fired.

15. The modular air sampling system of claim 14, wherein said shell casing is a 40 mm shell casing.

16. The modular air sampling system of claim 1, wherein the modular air sampling system is configured to fit into a conventional launch platform from which the modular air sampling system can be launched.

17. The modular air sampling system of claim 16, wherein the launch platform is a grenade launcher.

18. The modular air sampling system of claim 1, further comprising a launch platform for firing the modular air sampling system.

19. The modular air sampling system of claim 18, wherein the launch platform is a grenade launcher.

20. The modular air sampling system of claim 1, wherein the signal representative of sampled contaminants in the atmosphere is further representative of a concentration of the sampled contaminants in the atmosphere.

21. The modular air sampling system of claim 1, wherein the contaminants are selected from chemical contaminants and biological contaminants.

22. A modular air sampling system, comprising:

a sensor module having a housing, said sensor module including a sensor for sampling contaminants in the atmosphere;

processing electronics received within the housing in communication with the sensor for receiving a signal from the sensor representative of sampled contaminants in the atmosphere;

a radio frequency transmitter received within the housing and operably coupled to the processing electronics for transmitting a radio frequency signal representative of one or more contaminants sensed by the sensor; and a shell casing and a propelling charge contained within the shell casing for firing the modular air sampling system.

23. The modular air sampling system of claim 22, wherein the housing includes one or more inlets allowing ambient air to pass into the interior of the housing.

24. The modular air sampling system of claim 23, further comprising one or more air directing surfaces for directing ambient air into each of the one or more inlets.

25. The modular air sampling system of claim 22, further comprising:

one or both of a position sensor and a time-of-flight sensor received within the housing and operatively coupled to the processing electronics, said processing electronics configured to correlate one or both of a time and a geographic location with the signal from the sensor representative of sampled contaminants in the atmosphere.

26. The modular air sampling system of claim 22, wherein the rocket module is removably attached to the processing and sending module.

27. The modular air sampling system of claim 22, further comprising:

said shell casing attached to a rearward end of the sensor module, said shell casing including a charge of explosive material configured to propel the modular air sampling system a distance to a remote location to be sampled.

28. The modular air sampling system of claim 27, wherein said shell casing is a 40 mm shell casing.

29. The modular air sampling system of claim 22, wherein the modular air sampling system is configured to fit into a conventional launch platform from which the modular air sampling system can be launched.

30. The modular air sampling system of claim 29, wherein the launch platform is a grenade launcher.

31. The modular air sampling system of claim 22, further comprising a launch platform for firing the modular air sampling system.

32. The modular air sampling system of claim 31, wherein the launch platform is a grenade launcher.

33. The modular air sampling system of claim 22, wherein the signal representative of sampled contaminants in the atmosphere is further representative of a concentration of the sampled contaminants in the atmosphere.

34. The modular air sampling system of claim 22, wherein the contaminants are selected from chemical contaminants and biological contaminants.

35. A modular air sampling system, comprising:

a sensor module defining a nose, said sensor module including a sensor for sampling contaminants in the atmosphere;

a flight control module removably attached to the sensor module and containing a flight control system for guiding said air sampling system toward a target; and a processing and sending module removably attached to the flight control module, the processing and sending module including processing electronics in communication with the sensor for receiving a signal from the sensor representative of sampled contaminants in the atmosphere, said processing and sending module further including a radio frequency transmitter operably coupled to the processing electronics for transmitting a radio frequency signal representative of one or more contaminants sensed by the sensor.

36. The modular air sampling system of claim 35, wherein said flight control module includes a plurality of airfoils, said airfoils being moveable between a retracted state and an extended state.

* * * * *